United States Patent
Smith

(10) Patent No.: US 9,357,910 B2
(45) Date of Patent: Jun. 7, 2016

(54) WOUND RETRACTOR INCLUDING RIGID RING

(71) Applicant: Covidien LP, Mansfield, MA (US)

(72) Inventor: Robert C. Smith, Middlefield, CT (US)

(73) Assignee: Covidien LP, Mansfield, MA (US)

(*) Notice: Subject to any disclaimer, the term of this patent is extended or adjusted under 35 U.S.C. 154(b) by 42 days.

(21) Appl. No.: 13/755,156

(22) Filed: Jan. 31, 2013

(65) Prior Publication Data

US 2013/0225930 A1    Aug. 29, 2013

Related U.S. Application Data

(60) Provisional application No. 61/602,098, filed on Feb. 23, 2012.

(51) Int. Cl.

| | |
|---|---|
| A61B 1/32 | (2006.01) |
| A61B 1/24 | (2006.01) |
| A61B 1/303 | (2006.01) |
| A61B 1/31 | (2006.01) |
| A61B 1/313 | (2006.01) |
| A61B 17/34 | (2006.01) |
| A61B 17/02 | (2006.01) |
| A61B 17/00 | (2006.01) |

(52) U.S. Cl.
CPC ... *A61B 1/32* (2013.01); *A61B 1/24* (2013.01); *A61B 1/303* (2013.01); *A61B 1/31* (2013.01); *A61B 1/3132* (2013.01); *A61B 17/0293* (2013.01); *A61B 17/3423* (2013.01); *A61B 2017/00557* (2013.01)

(58) Field of Classification Search
USPC ................................................. 600/203–209
See application file for complete search history.

(56) References Cited

U.S. PATENT DOCUMENTS

| | | | |
|---|---|---|---|
| 7,052,454 B2 | 5/2006 | Taylor | |
| 7,998,068 B2 | 8/2011 | Bonadio et al. | |
| 8,021,296 B2 | 9/2011 | Bonadio et al. | |
| 2005/0267419 A1* | 12/2005 | Smith | 604/256 |
| 2006/0149306 A1 | 7/2006 | Hart et al. | |
| 2009/0221966 A1 | 9/2009 | Richard et al. | |
| 2012/0130186 A1 | 5/2012 | Stopek et al. | |
| 2012/0157779 A1 | 6/2012 | Fischvogt | |
| 2012/0209077 A1 | 8/2012 | Racenet | |

FOREIGN PATENT DOCUMENTS

| | | |
|---|---|---|
| EP | 1312318 A1 | 5/2003 |
| EP | 2044889 A1 | 4/2009 |
| WO | WO2010141673 | 12/2010 |

OTHER PUBLICATIONS

European Search Report dated Jul. 21, 2014 issued in European Application No. 13156293.

* cited by examiner

*Primary Examiner* — Sameh Boles

(57) ABSTRACT

A surgical apparatus for positioning within a tissue tract accessing an underlying body cavity adapts to tissue tracts of different widths. The surgical instrument includes a proximal member, a distal member, and a sleeve extending between the proximal member and the distal member and defining a longitudinal passage therein. The proximal member includes an inflatable member that selectively adjusts the radial dimension of the proximal member. A ring member may be separately insertable by a user during a surgical procedure into the space directly adjacent to the radially-inner surface of the inflatable member, so as to selectively provide rigidity to the proximal member.

17 Claims, 3 Drawing Sheets

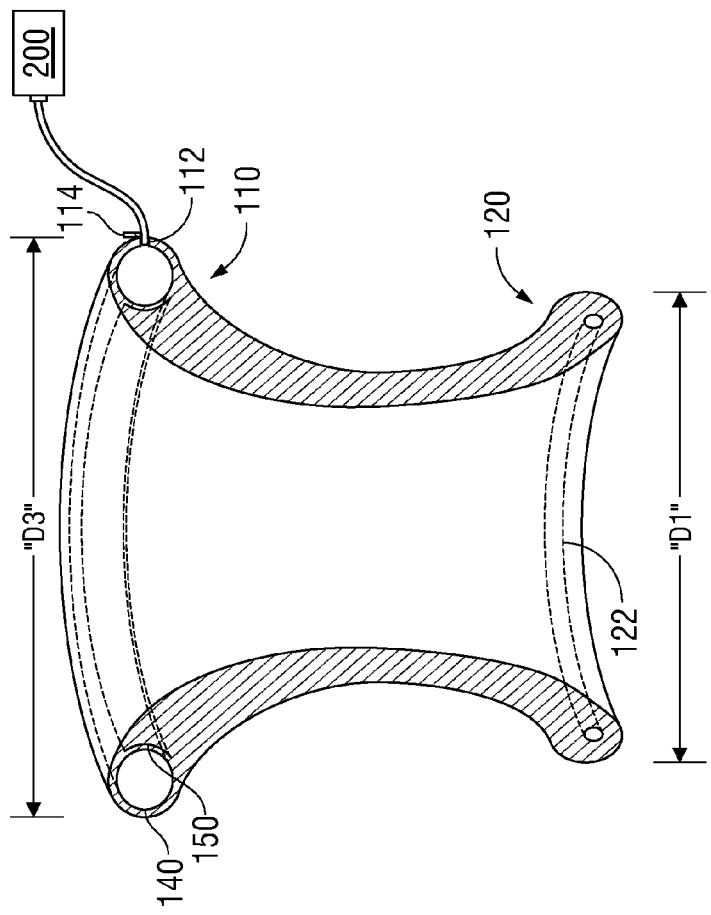
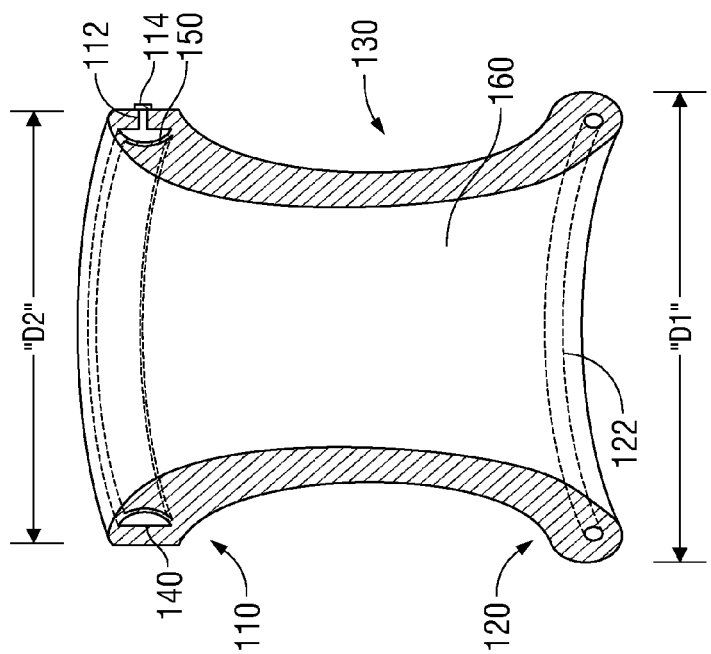

WOUND RETRACTOR INCLUDING RIGID RING

CROSS REFERENCE TO RELATED APPLICATION

The present application claims the benefit of and priority to U.S. Provisional Application Ser. No. 61/602,098, filed on Feb. 23, 2012, the entire contents of which are incorporated herein by reference.

BACKGROUND

1. Technical Field

The present disclosure relates generally to surgical apparatuses for use in minimally invasive surgical procedures, such as endoscopic and/or laparoscopic procedures, and more particularly, relates to wound retraction in these procedures.

2. Description of Related Art

Today, many surgical procedures are performed through small openings in the skin, as compared to large openings that are typically required in traditional procedures, in an effort to reduce trauma to the patient and reduce the patient's recovery time. Generally, such procedures are referred to as "endoscopic", unless performed on the patient's abdomen, in which case the procedure is referred to as "laparoscopic." Throughout the present disclosure, the term "minimally invasive" should be understood to encompass both endoscopic and laparoscopic procedures.

During a typical minimally invasive procedure, surgical instruments, such as endoscopes, graspers, staplers and forceps, are inserted into the patient's body through the opening in tissue. To protect the opening from accidental penetration by the surgical instruments, wound retractors are often placed across the opening.

Different openings have different depths and widths due to the needs of the procedures and the conditions of the tissues where the openings are created. For instance, the width of the opening depends on the procedure to be performed, and the depth of the opening may depend on the tissue thickness. For that reason, it is desirable to have a wound retractor that is adapted to retract openings of different widths and depths. Once the wound retractor is placed across an opening, it is also desirable to maintain the opening at its retracted position during the procedure in order to provide a consistent view of the target surgical site.

A typical wound retractor in the prior art is configured to have a particular radial dimension that is designed to fit an opening of a particular width. Wound retractors of different radial dimensions are designed for openings of different widths. There is no single wound retractor with adjustable radial dimension that adapts to fit openings of different widths. Further, the wound retractors in the prior art are also known for their drawbacks such as difficult placement and cumbersome use.

Based on the above, a continuing need exists for a wound retractor with increased ease of use and increased versatility to adapt to openings of different widths and depths.

SUMMARY

Disclosed herein is a surgical apparatus for positioning within a tissue tract accessing an underlying body cavity. The surgical apparatus includes a proximal member including an inflatable member adjustable to a plurality of radial dimensions, a distal member axially aligned with respect to the proximal member, and a flexible sleeve extending between the proximal and distal members and defining a passage for reception of object. A ring member may be separately insertable by a user during a surgical procedure into the space directly adjacent to the radially-inner surface of the inflatable member, so as to selectively provide rigidity to the proximal member.

In some embodiments, the proximal member, the distal member and the inflatable member each have an annular configuration.

The proximal member is configured to transit between a maximal radial dimension and a minimal radial dimension. The proximal member may include a rigid ring member defining a circumferential recessed portion for receiving the inflatable member. The inflatable member is configured to expand in a radial dimension. The rigid ring member and the inflatable member may be embedded within the proximal member or mounted to an outer circumferential surface of the proximal member.

In some embodiments, the distal member includes a deformable material, and has a constant radial dimension in a normal, unbiased condition. Further, the distal member may include a flexible ring member to maintain a constant radial dimension in a normal, unbiased condition.

Also disclosed is a method of retracting a tissue tract, including positioning a surgical apparatus within the tissue tract. The surgical apparatus includes a proximal member including an inflatable member adjustable to a plurality of radial dimensions, a distal member axially aligned with respect to the proximal member, and a flexible sleeve extending between the proximal and distal members and defining a passage for reception of object.

The method further includes inflating the inflatable member, selectively adjusting the radial dimension of the proximal member, and retracting the tissue tract.

The method may also include expanding the radial dimension of the proximal member during inflation, and increasing tension in the flexible sleeve to retract the tissue tract during inflation.

DESCRIPTION OF THE DRAWINGS

The above and other aspects, features, and advantages of the present disclosure will become more apparent in light of the following detailed description when taken in conjunction with the accompanying drawings in which:

FIG. 2A is a cross sectional view of the surgical apparatus of FIG. 1 illustrating an inflatable member in a deflated state mounted in a proximal member;

FIG. 2B is a cross-sectional view of the surgical apparatus of FIG. 2A illustrating the inflatable member in a maximally inflated state;

DETAILED DESCRIPTION

Figure 1:
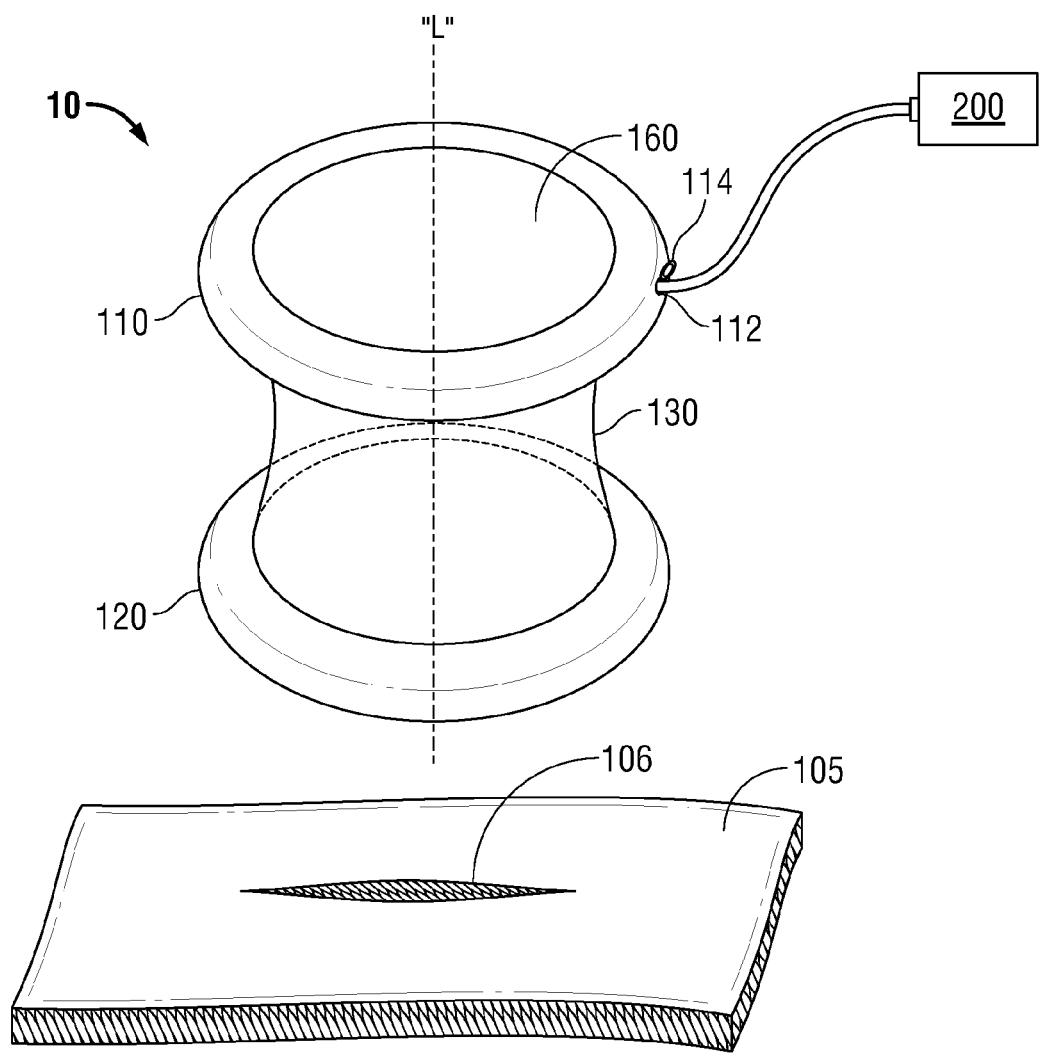
FIG. 1 is a front perspective view of a surgical apparatus in accordance with the principles of the present disclosure illustrating a surgical apparatus positioned relative to the tissue.

Particular embodiments of the present disclosure will be described herein with reference to the accompanying drawings. As shown in the drawings and as described throughout the following description, and as is traditional when referring to relative positioning on an object, the term "proximal" or "trailing" refers to the end of the apparatus that is closer to the user and the term "distal" or "leading" refers to the end of the apparatus that is farther from the user. In the following description, well-known functions or constructions are not described in detail to avoid obscuring the present disclosure in unnecessary detail.

Referring now to the drawings, in which like reference numerals identify identical or substantially similar parts throughout the several views, FIG. 1 illustrates a surgical apparatus 10 in accordance with the principles of the present disclosure. The surgical apparatus 10 is adapted for insertion into a tissue tract 105 through a tissue opening 106. The tissue opening 106 may be a single incision, e.g., through the abdominal or peritoneal lining, or a naturally occurring orifice (i.e. mouth, anus, or vagina). The surgical apparatus 10 will be described in greater detail hereinbelow.

As shown in FIG. 1, the surgical apparatus 10 defines a longitudinal axis "L," and includes a proximal member 110, a distal member 120, and a sleeve (lumen) 130 extending therebetween. The proximal member 110 and the distal member 120 are axially aligned along the longitudinal axis "L." Each of the proximal member 110 and the distal member 120 exhibits an annular or O-ring configuration. It is also envisioned that the proximal member 110 and the distal member 120 may exhibit other configurations.

The distal member 120 has a constant radial dimension of "D1," as illustrated in FIGS. 2A-2B, in a normal, unbiased condition. The distal member 120 is deformable to have a different radial dimension when placed in a biased condition, for instance, when placed under pressure. The distal member 120 has a resilient nature that returns itself to its normal radial dimension "D1" upon removal of the biased condition.

In certain embodiments, the distal member 120 is made from a semi-rigid material. It is also envisioned that the distal member 120 is made from a semi-resilient, disposable, compressible and flexible type (e.g. rubber or sponge) material, for example, but not limited to, a suitable foam, gel material, or soft rubber having sufficient compliance to be reduced to a small dimension for insertion through a small opening. In one embodiment, the foam includes a polyisoprene material. It is also envisioned that the distal member 120 may include a deformable, elastomeric and/or resilient material.

The distal member 120 may also be made from a flexible material such as metal or plastic. The flexible nature of the distal member 120 provides an easy insertion and removal of the surgical apparatus 10 through the tissue tract 105. Specifically, the flexible nature of the distal member 120 easily adapts to different configurations in the presence of biasing factors, such that the distal member 120 can be easily deformed when manipulated by a surgeon or when pressed by the tissue opening 106 during insertion into the tissue tract 105. Under these circumstances, the distal member 120 transits from its normal shape to a distorted shape. The resilient material in the distal member 120 enables it to resume its normal shape in the absence of any biasing factors.

Further, the distal member 120 may include a ring member 122 therein, as illustrated in FIGS. 2A-2B. The ring member 122 may include a flexible material with a degree of rigidity slightly greater than that of the distal member 120. The ring member 122 serves to stabilize the distal member 120 and facilitates the distal member 120 to maintain its normal radial dimension. The ring member 122 may be embedded entirely within the distal member 120 or mounted to the outer circumferential surface of the distal member 120. It is envisioned that the ring member 122 may be permanently attached to the distal member 120 by glue, suture, or by an overmolding process.

The proximal member 110 may include a material identical or similar to that of the distal member 120 which provides the proximal member 110 with a flexible, deformable and resilient nature.

Further, the proximal member 110 includes an expandable assembly which selectively adjusts the radial dimension of the proximal member 110. Specifically, the expandable assembly defines a plurality of states each corresponding to a different radial dimension of the proximal member 110. The plurality of states includes a maximally contracted state in which the radial dimension of the proximal member 110 is minimized, and a maximally expanded state in which the radial dimension of the proximal member 110 is maximized, and other states between the maximally contracted state and the maximally expanded state which correspond to different radial dimensions between the minimal and maximal radial dimensions. With an adjustable radial dimension, the proximal member 110 can adapt to different tissue openings of different widths.

In one embodiment, as illustrated in FIG. 2A-2B, the expandable assembly includes an inflatable member 140, such as a balloon. The inflatable member 140 has an annular configuration. The inflatable member 140 defines a port 112 therein for connection to an inflation source 200 which delivers an inflation medium to the inflatable member 140. It is also envisioned that the port 112 may be connected to an evacuation source which withdraws the inflation medium from the inflatable member 140. The inflatable member 140 includes an inflatable material which is configured to expand in a radial dimension upon inflation. Deflation and inflation of the inflatable member 140 selectively adjusts the radial dimension of the inflatable member 140, which, in turn, selectively adjusts the radial dimension of the proximal member 110. For instance, in a completely deflated state as illustrated in FIG. 2A, the proximal member 110 has a minimal radial dimension of "D2." By contrast, in a maximally inflated state as illustrated in FIG. 2B, the proximal member 110 has a maximal radial dimension of "D3" which is significantly larger than "D2."

FIG. 2A illustrates that the proximal member 110 has a minimal radial dimension "D2" that is smaller than the radial dimension "D1" of the distal member 120. In other embodiments, the proximal member 110 may have a minimal radial dimension that is larger than or similar to the radial dimension "D1" of the distal member 120.

The inflation source includes a control mechanism that allows the surgeon to selectively control the amount of the inflation medium that enters or leaves the inflatable member 140, so as to adjust the radial dimension of the proximal member 110 accordingly. Inflation or deflation stops when the proximal member 110 reaches a desired radial dimension. The proximal member 110 includes a lid 114 hingedly attached to the proximal member 110. The lid 114 is disposed on the proximal member 110 in a manner to close and open the port 112. In its closed state as illustrated in FIG. 2A, the lid 114 prevents the inflation medium communicating through the port 112 to maintain the proximal portion 110 at a desired radial dimension. When the lid 114 is in an open state as illustrated in FIG. 2B, the port 112 may be connected to the insufflations source 200 to inflate the inflatable member 140. It is contemplated that the lid 114 may be replaced by a valve as is known in the art.

The inflatable member 140 may be embedded entirely within the flexible material of the proximal member 110, as illustrated in FIGS. 2A-2B. Alternatively, the inflatable member 140 may be mounted to an outer circumferential surface of the proximal member 110. In either embodiment, the inflatable member 140 is attached to the flexible material of the proximal member 110. Inflation of the inflatable member 140 causes the flexible material attached thereto to expand radially outwardly, and gradually enlarges the radial dimension of the proximal member 110. Similarly, deflation of the inflatable member 140 causes the flexible material attached thereto to contract radially inwardly, and gradually reduces the radial dimension of the proximal member 110.

It is envisioned that the inflatable member 140 may be permanently attached to the proximal member 110 by glue, suture, or by an overmolding process.

Figure 3A:
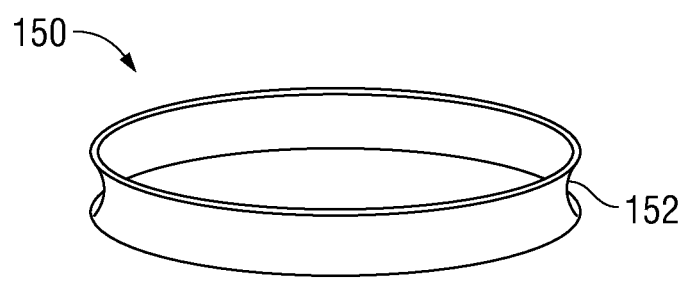
FIG. 3A is a perspective view of a rigid ring member of the surgical apparatus of FIG. 2A.
Figure 3B:
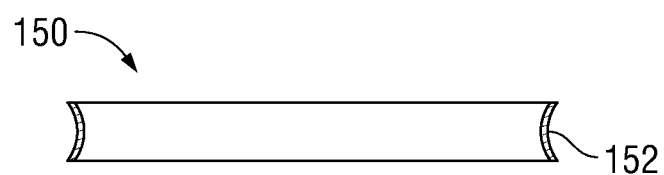
FIG. 3B is a cross-sectional view of the rigid ring member of FIG. 3A.

In some embodiments, in addition to the inflatable member 140, the proximal member 110 may include a ring member 150 as seen in FIGS. 2A-2B. The ring member 150 has a concave or "C"-shaped cross-sectional profile as illustrated in FIGS. 3A-3B. The ring member 150 defines an outer circumferential recessed portion 152 for receiving the inflatable member 140 therein, such that the inflatable member 140 can be placed circumferentially about the ring member 150 and in abutting relation with the ring member 150. The ring member 150 includes a rigid material and has a radial dimension corresponding to the minimal radial dimension of the proximal member 110. Due to its rigid characteristics, the ring member 150 ensures that the proximal member 110 does not contract any further below its minimal radial dimension during deflation. Since the ring member 150 is placed circumferentially within the inflatable member 140, the ring member 150 can effectively prevent the inflatable member 140 from expanding in a radially inward direction during inflation, which, in turn, forces the inflatable member 140 to expand in a radially outwardly direction upon inflation.

The ring member 150 and the inflatable member 140 may together be embedded within the proximal member 110. Alternatively, they may be mounted to an outer circumferential surface of the proximal member 110. They together may be permanently attached to the proximal member 110 by glue, suture, or by an overmolding process. Alternatively, the ring member 150 may be separately insertable by a user during a surgical procedure into the space directly adjacent to the radially-inner surface of the inflatable member, so as to selectively provide rigidity to the proximal member 110 when desired.

In some embodiments, it is envisioned that the expandable assembly of the proximal member 110 may comprise some other mechanical spreaders, in lieu of the inflatable member 140, to selectively vary the radial dimension of the proximal member 110.

The sleeve 130 defines a longitudinal passage 160 extending between the proximal member 110 and the distal member 120, which allows objects, e.g. surgical instruments, surgeon's hands, organs removed from beneath the tissue tract 105, to pass therethrough. As shown in FIG. 1, the sleeve 130 exhibits a generally hour-glass configuration. However, it is contemplated that the sleeve 130 may define other configurations, e.g. a generally cylindrical shape, both prior and subsequent to insertion within the tissue tract 105.

The sleeve 130 may include a material identical or similar to that of the distal member 120 and/or the proximal member 110 which provides the sleeve 130 with a flexible, deformable and resilient nature. Additionally, the sleeve 130 may include a material that establishes a sealing relation with the tissue tract 105 when the sleeve 130 is disposed across the tissue tract 105.

It is envisioned that the proximal member 110, the distal member 120 and the sleeve 130 each being permanently attached to the other by glue, suture, or by an overmolding process. In some embodiments, they are all monolithically integrated to form a unitary structure.

In operation, the surgeon first deforms the distal member 120 to a smaller dimension for insertion into a tissue opening 106. Once the distal member 120 is placed immediately beneath the tissue tract 105, the distal member 120 resumes its normal radial dimension "D1". The surgeon then adjusts the expandable assembly, i.e., the inflatable member 140, through inflation and/or deflation until the proximal member 110 reaches a desired radial dimension, at which point the sleeve 130 snugly fits against the tissue tract 105 and retracts the tissue tract 105 to an ideal extent.

In use, the present invention enables wound protection while allowing adjustability to suitably fit within openings of different dimensions. For instance, the proximal member 110 with its selectively varying radial dimension adapts to openings of different widths. Further, variation of the proximal member 110 in its radial dimension creates different degrees of tension in the sleeve 130 along the longitudinal dimension "L", which, in turn, causes the sleeve 130 to suitably retract openings of different depths.

Furthermore, the expandable assembly of the proximal member 110, i.e., the inflatable member 140, can securely maintain the proximal member 110 at a selected radial dimension, to provide a surgeon a consistent view of the target surgical site.

Additionally, the sleeve 130 is configured to conform to the opening and protects the tissue opening 106 from infectious tissue.

Further, the flexible nature of the distal member 120 allows the distal member 120 to be easily manipulated to suit openings of different dimensions, and the resilient nature allows the distal member 120 to assume its original shape against the inside of the abdominal wall after insertion.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Different embodiments of the disclosure may be combined with one another based on the particular needs of the patients to achieve optimal results of the surgical procedures. Those skilled in the art will envision other modifications within the scope and spirit of the claims appended hereto.

What is claimed is:

1. A surgical apparatus for positioning within a tissue tract accessing an underlying body cavity, the surgical apparatus comprising:
   a proximal member including an inflatable member, the inflatable member adjustable to a plurality of radial dimensions;
   a distal member axially aligned with respect to the proximal member;
   a flexible sleeve extending between the proximal and distal members and defining a passage for reception of an object; and
   a ring member that is separately insertable by a user during a surgical procedure such that the inflatable member circumferentially surrounds the ring member, so as to selectively provide rigidity to the proximal member.

2. The surgical apparatus according to claim 1, wherein the proximal member has an annular configuration.

3. The surgical apparatus according to claim 1, wherein the distal member has an annular configuration.

4. The surgical apparatus according to claim 1, wherein the inflatable member has an annular configuration.

5. The surgical apparatus according to claim 1, wherein the inflatable member is embedded within the proximal member.

6. The surgical apparatus according to claim 1, wherein the inflatable member is mounted to an outer circumferential surface of the proximal member.

7. The surgical apparatus according to claim 1, wherein the inflatable member is configured to expand in a radial dimension.

8. The surgical apparatus according to claim 1, wherein the proximal member is configured to transit between a maximal radial dimension and a minimal radial dimension.

9. The surgical apparatus according to claim 1, wherein the distal member includes a deformable material.

10. The surgical apparatus according to claim 1, wherein the distal member has a constant radial dimension in a normal, unbiased condition.

11. The surgical apparatus according to claim 1, wherein the distal member includes a flexible ring member to maintain a constant radial dimension in a normal, unbiased condition.

12. The surgical apparatus according to claim 1, further comprising an inflation source to deliver an inflation medium to the inflatable member.

13. The surgical apparatus according to claim 1, wherein the flexible sleeve has a proximal end attached to the proximal member.

14. The surgical apparatus according to claim 1, wherein the inflatable member is adjustable in a radial direction.

15. A surgical apparatus for positioning within a tissue tract accessing an underlying body cavity, the surgical apparatus comprising:
- a proximal member including:
  - an inflatable member adjustable to a plurality of radial dimensions; and
  - a rigid ring member defining a circumferential recessed portion for receiving the inflatable member therewithin;
- a distal member axially aligned with respect to the proximal member; and
- a flexible sleeve extending between the proximal and distal members and defining a passage for reception of an object.

16. The surgical apparatus according to claim 15, wherein the flexible sleeve has a proximal end attached to the proximal member.

17. The surgical apparatus according to claim 15, wherein the inflatable member is adjustable in a radial direction.

* * * * *